(12) United States Patent
Keeton et al.

(10) Patent No.: US 8,459,120 B2
(45) Date of Patent: Jun. 11, 2013

(54) METHOD AND APPARATUS FOR AUTOMATED ULTRASONIC INSPECTION

(75) Inventors: Paul Ivan John Keeton, Woodbridge, VA (US); Sushma Kalavagunta, Burke, VA (US)

(73) Assignee: Sonix, Inc., Springfield, VA (US)

( * ) Notice: Subject to any disclaimer, the term of this patent is extended or adjusted under 35 U.S.C. 154(b) by 350 days.

(21) Appl. No.: 12/940,202

(22) Filed: Nov. 5, 2010

(65) Prior Publication Data
US 2012/0111118 A1    May 10, 2012

(51) Int. Cl.
*G01N 29/04* (2006.01)

(52) U.S. Cl.
USPC .................................. 73/620; 73/618; 73/644

(58) Field of Classification Search
USPC ............................. 73/620, 618, 628, 633, 644
See application file for complete search history.

(56) References Cited

U.S. PATENT DOCUMENTS

| | | | |
|---|---|---|---|
| 4,518,992 A | 5/1985 | Kessler et al. | |
| 4,781,067 A | 11/1988 | Cichanski | |
| 4,866,986 A | 9/1989 | Cichanski | |
| 5,481,202 A * | 1/1996 | Frye, Jr. ................... | 324/750.23 |
| 5,600,068 A | 2/1997 | Kessler et al. | |
| 5,684,252 A | 11/1997 | Kessler et al. | |
| 6,032,534 A | 3/2000 | Sherwin | |
| 6,357,136 B1 | 3/2002 | Erickson et al. | |
| 6,460,414 B1 | 10/2002 | Erickson et al. | |
| 6,587,981 B1 * | 7/2003 | Muradali et al. ............. | 714/726 |
| 6,880,387 B2 | 4/2005 | Kessler et al. | |
| 6,890,302 B2 | 5/2005 | Oravecz et al. | |
| 6,895,820 B2 | 5/2005 | Oravecz et al. | |
| 6,912,908 B2 | 7/2005 | Kessler et al. | |
| 6,981,417 B1 | 1/2006 | Oravecz | |
| 7,000,475 B2 | 2/2006 | Oravecz et al. | |
| 7,013,732 B2 | 3/2006 | McKeon | |
| 7,100,449 B2 | 9/2006 | Busch et al. | |
| 7,131,333 B2 | 11/2006 | Busch | |
| 7,181,969 B2 | 2/2007 | Busch et al. | |
| 7,395,713 B2 | 7/2008 | Kessler et al. | |
| 7,522,780 B2 | 4/2009 | Oravecz et al. | |
| 7,530,271 B2 | 5/2009 | Busch et al. | |
| 7,584,664 B2 | 9/2009 | Kessler | |
| 7,661,315 B2 | 2/2010 | Busch et al. | |
| 8,087,298 B1 * | 1/2012 | DiMambro et al. ............ | 73/629 |
| 2007/0012115 A1 | 1/2007 | Busch et al. | |
| 2008/0006091 A1 | 1/2008 | McKeon | |

OTHER PUBLICATIONS

Korean Intellectual Property Office, PCT International Search Report and Written Opinion, PCT Appl. PCT/2011/058000, mailed on May 29, 2012.

* cited by examiner

*Primary Examiner* — J M Saint Surin (57) ABSTRACT

A method and apparatus for ultrasonic inspection of one or more parts, in which one or more parts to be inspected are transferred from a parts carrier to a scan nest that is located in the scanning station. The parts are restrained in the scan nest and then scanned. A pick and place mechanism is used to transfer the parts to be inspected between the parts carrier the scan nest. The inspection path may be altered if a missing part is detected. In one embodiment, a first gas flow port located on the pick and place mechanism or on the transducer holder is used to blow ultrasonic coupling fluid from the front surface of the parts in the scan nest after they have been scanned. In a further embodiment, two or more scan nests are used for parallel operation.

54 Claims, 8 Drawing Sheets

FIG. 11

METHOD AND APPARATUS FOR AUTOMATED ULTRASONIC INSPECTION

BACKGROUND

Ultrasound has been used for non-destructive inspection of parts for many years. In the ultrasonic scanning of shafts or tubes, the part is rotated about its axis of symmetry while an ultrasonic transducer is moved parallel to the axis (i.e. along the shaft or tube) to complete a scan and detect flaws in the part. More recently, ultrasonic inspection has been extended to small parts, such as integrated circuits or other electronic components. Positioning and scanning of individual small parts may be too time-consuming for production line testing. However, the parts are often loosely arranged in trays or carriers to facilitate transfer of the parts through the production process. Scanning of the parts in trays speeds up the inspection process but requires special apparatus to hold the parts in place while they are immersed in an acoustic coupling fluid or subjected to a flow of coupling fluid. Additional apparatus is required to dry the parts after they have been scanned. In prior approaches, the scan itself is usually performed by moving the tray of parts in a series of steps in one direction while an ultrasonic transducer is moved in a perpendicular direction. In this way a raster scan of each part is performed on a rectangular grid.

A disadvantage of this approach is that both the parts and the tray become wet and are difficult to dry. This problem becomes worse as the size of the parts becomes smaller.

A further disadvantage is that parts may become dislodged from the tray. Dislodged parts must be detected before a scan is made.

A further disadvantage is the need for a mechanism for accurately moving the tray through the scanning station.

A further disadvantage is that wet trays may slip on the conveyor belts used for transporting the trays.

A further disadvantage is that the trays become warped over time, so that the parts are not accurately aligned in the same plane. Motion of the transducer perpendicular to the scanning plane is required to compensate for the warping.

A still further disadvantage is that some trays hold the parts in deep wells, which necessitates an increased distance between the transducer and the parts during scanning. This degrades the scan image.

An alternative approach, applicable to larger parts such as fabrication wafers, is to scan each part individually. In this approach, a wafer is held stationary in a wafer chuck and an ultrasound transducer is moved in a scan pattern across the surface of the wafer. A robot arm may be used to move a series of wafers, one at a time, from a wafer holder to a scan station and back again.

BRIEF DESCRIPTION OF THE FIGURES

The accompanying figures, in which like reference numerals refer to identical or functionally similar elements throughout the separate views and which together with the detailed description below are incorporated in and form part of the specification, serve to further illustrate various embodiments and to explain various principles and advantages all in accordance with the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to ultrasonic imaging and automated control inspection. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Figure 1:
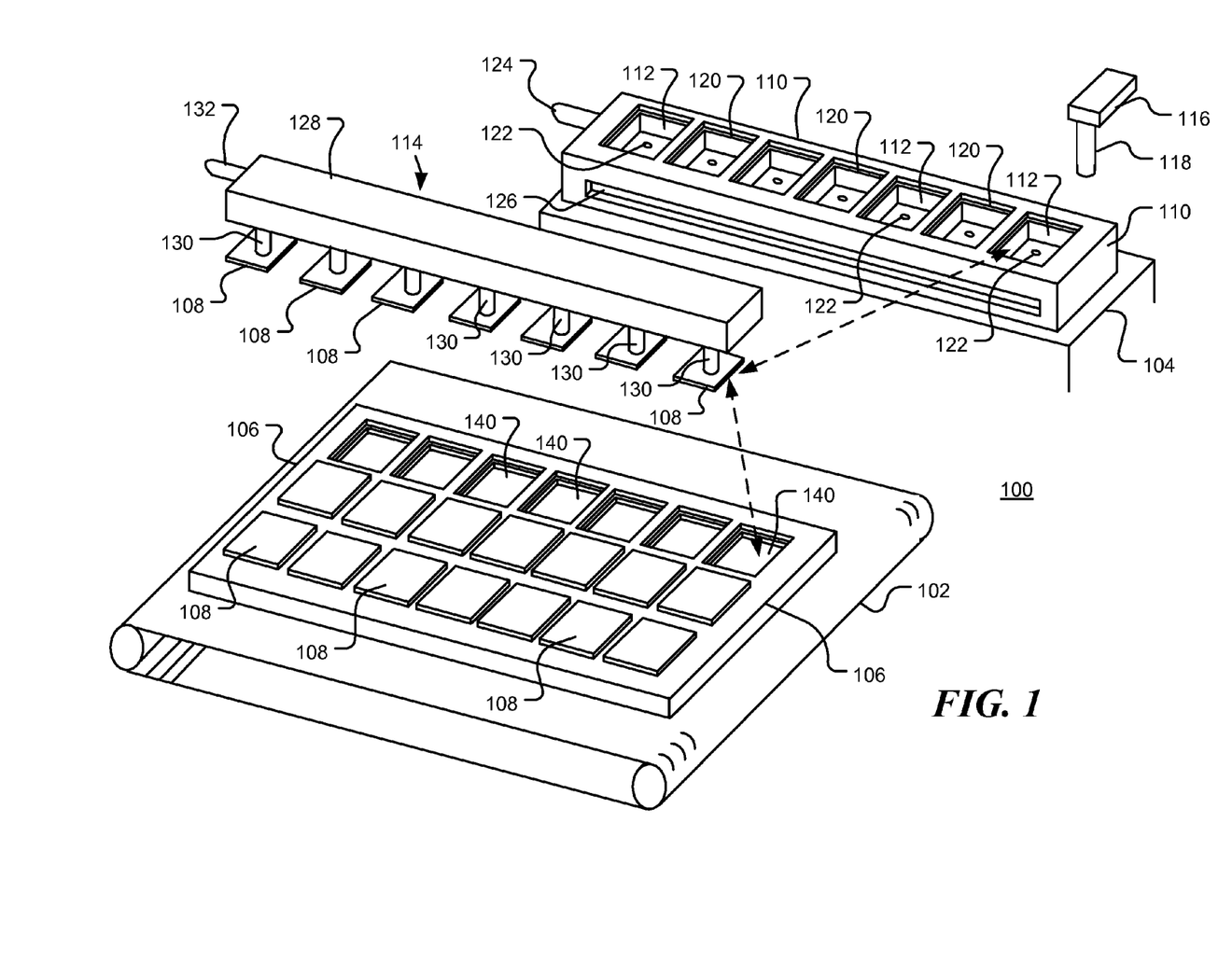
FIG. 1 is a diagrammatic representation of an exemplary ultrasonic inspection system consistent with some embodiments of the invention.

FIG. 1 is a diagrammatic representation of an exemplary ultrasonic inspection system in accordance with some embodiments of the invention. Referring to FIG. 1, the ultrasonic inspection system 100 includes a transfer station 102 and scanning station 104. The transfer station 102 accommodates a parts carrier 106 for carrying one or more parts 108, such as integrated circuits, to be inspected. A first scan nest 110, located in the scanning station 104, is used for holding parts while they are inspected, and may include a plurality of receptacles 112 for accommodating the parts during inspection.

A pick and place mechanism 114 is provided for transferring the plurality of parts 108 to be inspected between the parts carrier 106 in the transfer station 102 and the first scan nest 110. When the parts are held in the scan nest 110, an ultrasonic scanner 116, that includes one or more ultrasonic transducers 118, is moved in a controlled path to scan the parts held in the first scan nest 110.

In the embodiment shown in FIG. 1, the scan nest 110 comprises a linear arrangement of receptacles 112 into which parts to be scanned may be placed. The receptacles are sized such that a part to be scanned is supported at its periphery by a ledge 120 around the edge of a well of the receptacle 112. A port 122 in each well allows air to be drawn from the well through outlet 124. This creates a pressure difference across the front (exposed) and back surfaces of the part that tends to hold the part in place while the part is scanned. A slot 126 may be provided to allow access to the underside of the scan nest.

A compliant material may be placed on the ledge 120 around the edge of a well of the receptacle 112 to improve the seal between the part and the ledge. The seal is improved because the compliant material deforms to match the shape contours of the underside of the part.

In further embodiments, a clamping force, applied at one or more edges of the part, is used to hold the part in place. Many clamping mechanisms are known to those of ordinary skill in the art, including, for example, spring, piezoelectric, pneumatic, hydraulic and magnetic clamps.

The pick and place mechanism 114 comprises a robotic manipulator (not shown) that allows parts 108 to be moved under automatic control between the transfer station 102 and the scanning station 104. In the embodiment shown in FIG. 1, the pick and place mechanism 114 incorporates a vacuum manifold 128 and has one or more vacuum heads 130. In the figure the vacuum heads are shown holding parts 108. Air is drawn from the vacuum manifold through outlet 132 using a vacuum pump, for example. In operation, the robotic manipulator is controlled to move the lower tips of the vacuum heads 130 into contact with parts 108 in the parts carrier 106 or the scan nest 110. In one embodiment, the vacuum heads 130 include a vacuum saver valve. In the event that a vacuum head 130 fails to contact and seal with a part, the vacuum saver valve is closed, so that a vacuum is maintained within the vacuum manifold 128.

In one embodiment, the vacuum heads 130 are spaced to align with a particular arrangement of parts 108 in a parts carrier 106. Optionally, the vacuum saver valves are instrumented so that a signal is generated by a signal generator to indicate if a valve is open or closed. A closed valve may be indicative of a missing part or a failed pick-up. This signal is supplied to the scanning station and, if a part is missing, the scan path may be altered to avoid wasting time scanning empty receptacles in the scan nest 110. Also, the signal may be used to generate an alert, as in the case of a failed pick-up, for example.

In a further embodiment, a larger number of closely spaced vacuum heads 130 may be used, the spacing being chosen such that at least one vacuum head 130 aligns with each part 108 for a variety of different part sizes and part spacing in the parts carrier 106. In such an arrangement, there is an increased chance that some vacuum heads 130 will not contact parts, so vacuum saver valves may be used.

The pick and place mechanism 114 may use computer vision to find parts at unknown positions in the parts carrier 106. High resolution vision hardware may be used together with image analysis tools. These image analysis tools may be integrated into the control software of the pick and place mechanism, such that an image analyzer is in communication with control software of the pick and place mechanism. For example, in one embodiment, linear motor actuators move the pick and place mechanism 114 in the horizontal plane to align a vacuum head with a part and the vacuum head is then lowered to pick up the part.

In one embodiment, a missing part is detected by forming an image of the parts, in the parts carrier or the scan nest, using a computer vision system, and analyzing the image to detect parts that are present.

In a further embodiment, a missing part is detected by forming an image of the parts, in the parts carrier or the scan nest, using a computer vision system, and analyzing the image to detect empty locations in the parts carrier or scan nest.

In a still further embodiment, a missing, or out of place, part is detected by performing an initial ultrasonic scan of parts in the scanning station. The initial ultrasonic scan comprises at least one ultrasonic measurement for each expected part location in the scanning station. If a pulse-echo measurement is made, locations where a part is missing will have a much smaller response than locations where a part is present. Missing parts may be detected by comparing the ultrasonic measurements made at different locations to an expected ultrasonic measurement. The expected measurement may be, for example, related to the median response level or it may be predetermined. An unexpected response may also be recorded when a part is tilted or out of place, Similarly, with a through-transmission measurement, missing parts may be detected by comparing the ultrasonic measurements made at different locations to an expected ultrasonic measurement.

Various actions may be taken if a part is found to be missing or displaced. For example, the operator may be alerted, or the scan path altered, or the scan may be aborted.

The parts carrier 106 may be a JEDEC tray, an Auer boat, a strip, or other carrier. A JEDEC tray, for example, has a number of receptacles 140 in which parts may be carried. The parts carrier 106 may be moved into the transfer station 102 using a conveyor system, such as a conveyor belt, for example. As indicated by the broken arrows shown in FIG. 1, the parts 108 held by the pick and place mechanism 114 may be automatically transferred from the parts carrier 106 to the scan nest 110, scanned, and then returned either to the parts carrier or a drying station or to some other location. Transferring parts from the part carrier to the scan nest is taken to include releasing the parts from the parts carrier, if necessary.

Figure 2:
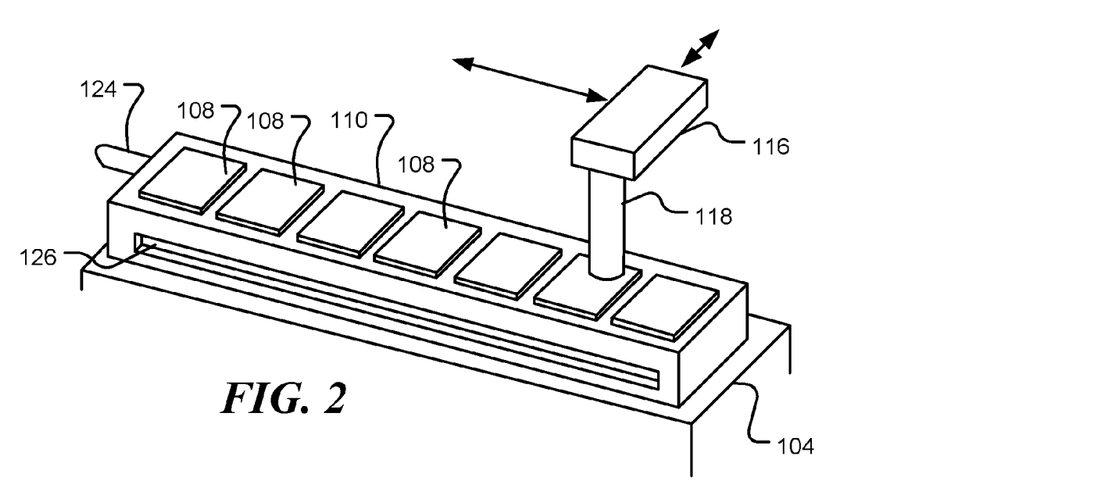
FIG. 2 is a diagrammatic view of an exemplary scanning station in accordance with some embodiments of the invention.

In FIG. 1, the parts 108 are shown in parts carrier 106 or held by the pick and place mechanism 114. The scan nest 110 is empty. In operation, the pick and place mechanism 114 transfers a group of one or more parts from the parts carrier 106 to the scan nest 110, as shown in FIG. 2. FIG. 2 is a diagrammatic view of an exemplary scanning station in accordance with some embodiments of the invention. When in the scan nest 110, as shown in FIG. 2, the parts 108 are positioned such that the upper surfaces of the parts are substantially coplanar in a first plane. This may be a horizontal plane, as shown in the figure, or a sloped plane. This facilitates scanning of the parts. The scan nest 110 may be manufactured to a high degree of accuracy, such that when the parts are in the scan nest, the exposed surfaces of the parts are very close to being in the same plane. In contrast, parts in a carrier, such as a JEDEC tray, may be at different heights due to warping of the tray during use, making scanning more difficult. When the surfaces are substantially in the same plane, an ultrasonic transducer 118 may be moved in a scan path very close to the surface of the parts 108, thereby increasing the amount of ultrasonic energy coupled to the part, which in turn, improves the quality of the resulting scan image.

FIG. 2 depicts a single transducer 118, as might be used in pulse-echo scan where the ultrasound reflected from the part is collected and analyzed. In an alternative embodiment, a second transducer underneath the parts 108 may be used so allow through-transmission inspection. The second transducer may be located at the end of a thin support member or 'wand' that is passed through opening 126 in the scan nest. In this embodiment a clamping mechanism may be used to secure the parts 108 in the scan nest 110.

Multiple transducers may be used on either side of the part.

The one or more receptacles 112 of the scan nest 110 may be arranged in various patterns. When arranged linearly, as shown in FIG. 2, the ultrasonic transducer 118 may be moved, by a scanning mechanism (such as a robotic arm, for example), in a series of linear scan paths along the length (the longer dimension) of the scan nest, this being quicker than scanning across the width of the scan nest since fewer changes of direction are required.

Figure 3:
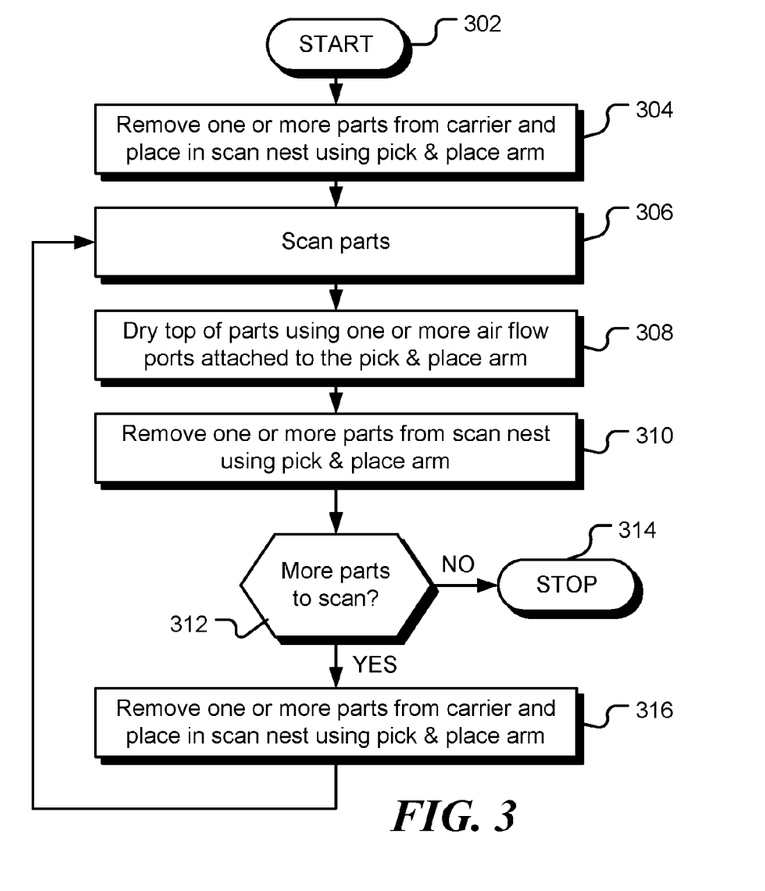
FIG. 3 is a flow chart of a method for automated ultrasonic inspection consistent with certain embodiments of the invention.

FIG. 3 is flow chart of a method for automated ultrasonic inspection consistent with certain embodiments of the invention. Following start block 302 in FIG. 3, at block 304 a group of one or more parts is removed from a parts carrier and placed in a scan nest using a pick and place mechanism. At block 306, an ultrasonic scan of the group of parts is performed, using coupling fluid to couple sound between an ultrasonic transducer and a surface of a part in the group of parts. The coupling fluid may be provided by a bubbler or by a fluid coupler, or by other methods known to those of ordinary skill in the art. At block 308, coupling fluid is blown from the exposed surface of the parts using a flow of gas, and, at block 310, the group of parts is removed from the scan nest, again using the pick and place mechanism. The gas may be nitrogen, for example, or a mixture of gases, such as air or nitrogen enriched air. The gas may be heated to improve drying. The flow of gas is generated from a gas flow port, such as a gas knife, nozzle or point jet. The gas flow port may be located on the robotic arm of the pick and place mechanism, on the same robotic arm as the ultrasonic transducer, or on a separate robotic arm. The gas flow from the gas flow port may be moved across the parts in the scan nest in linear or raster-scan path, for example. At decision block 312, a check is made to determine if more parts are to be scanned. If no more parts are to be scanned, as depicted by the negative branch from decision block 312, the method terminates at block 314. If more parts are to be scanned, as depicted by the positive branch from decision block 312, the next group of one or more parts is transferred from the parts carrier to the scan nest ready for scanning Flow then returns to block 306, where the group of parts in the scan nest is scanned.

The elements 308, 310, 312 and 316 relate to the unloading and reloading of parts in the scan nest. When a single scan nest is used, these elements cannot be performed concurrently with the scanning process. This limits the minimum time for inspecting a batch of parts. However, if a second scan nest is used, the parts in one scan nest may be scanned while the parts in the other scan nest are being unloaded or reloaded. This may increase the throughput of the inspection system. The method is illustrated in the flow chart of FIG. 4.

Figure 4:
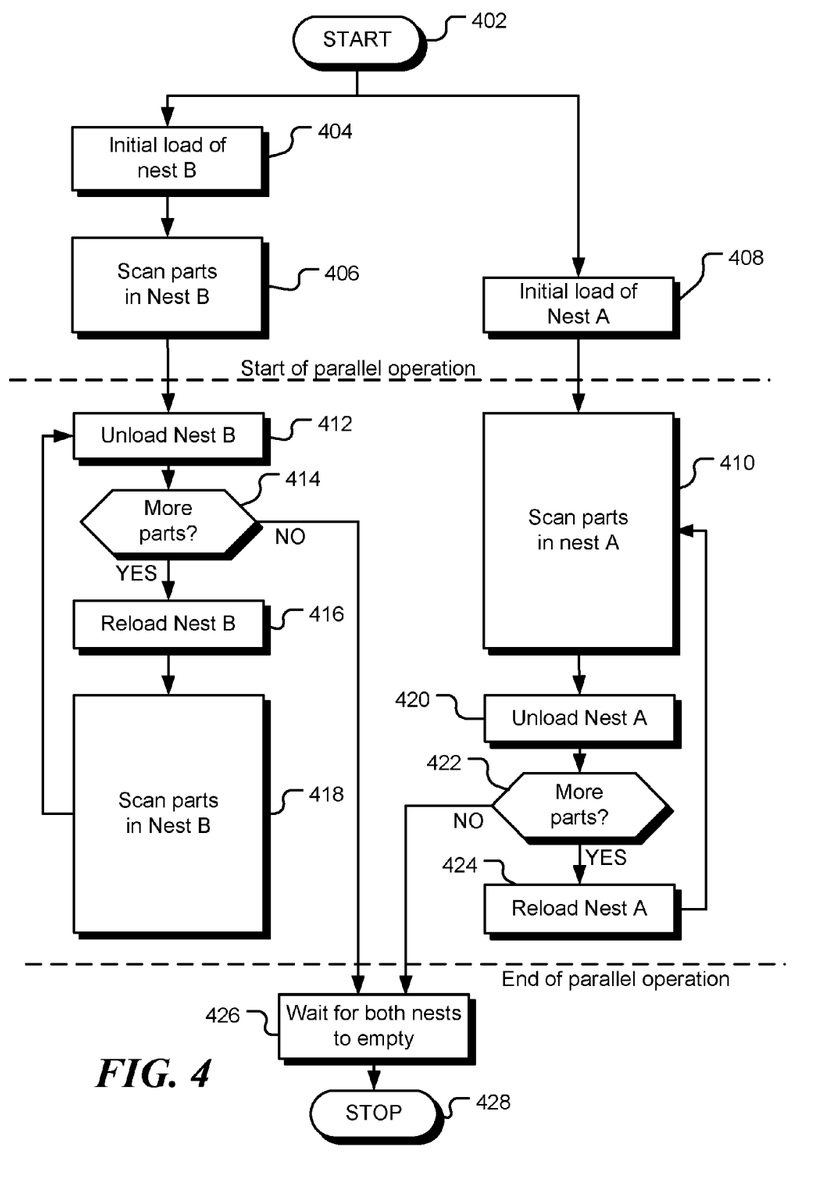
FIG. 4 is a flow chart of a further method for automated ultrasonic inspection consistent with certain embodiments of the invention.

Following start block 402 in FIG. 4, a second scan nest (nest B, say) is loaded with a group of one or more parts to be scanned at block 404 and the parts are scanned at block 406. While the parts in nest B are being scanned, the next group of parts to be scanned is loaded into the first scan nest (nest A) at block 408. Once blocks 406 and 408 are completed, parallel operation begins.

During a first time period, the ultrasonic scanner scans parts in the first scan nest (nest A), as depicted by block 410, and, during the same time period, the pick and place mechanism transfers parts between the second scan nest (nest B) and the parts carrier, as depicted by blocks 412, 414 and 416. In particular, scan nest B is unloaded at block 412 and if more parts are to be scanned (as depicted by the positive branch from decision block 414) the parts are loaded into scan nest B at block 416.

During a second time period, the ultrasonic scanner scans parts in the second scan nest (nest B), as depicted by block 418, and, during the same time period, the pick and place mechanism transfers parts between the first scan nest (nest A) and the parts carrier, as depicted by blocks 420, 424 and 426. In particular, scan nest A is unloaded at block 420 and if more parts are to be scanned (as depicted by the positive branch from decision block 422) the parts are loaded into scan nest A at block 424.

If there are no more parts to be scanned, as depicted by the negative branches from decision blocks 414 and 422, flow continues to block 426, where the system waits until both scan nests have been emptied. The method terminates at block 428.

Using two scan nests in the fashion described in FIG. 4, enables the throughput of the inspection system to be doubled compared to the use of a single scan nest.

Figure 5:
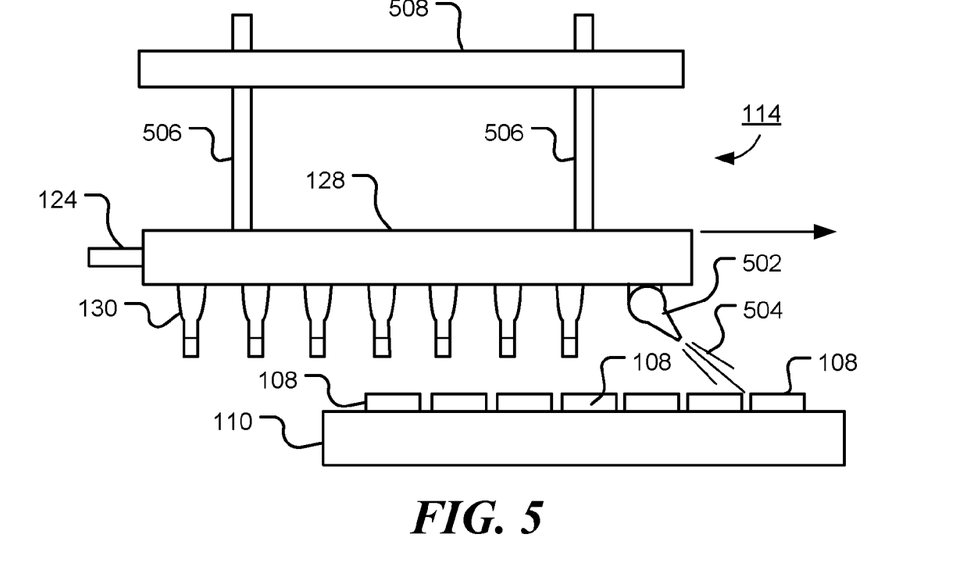
FIG. 5 is a diagrammatic view of a scan nest and a first gas flow port in accordance with some embodiments of the invention.

FIG. 5 is a diagrammatic view of a scan nest and a gas flow port in accordance with some embodiments of the invention. During ultrasonic scanning of the parts 108 in scan nest 110, a coupling fluid, such as water, may be used to improve the coupling of ultrasonic energy between the one or more ultrasonic transducers and the parts 108. Thus, the parts are wet when the scanning is completed. Coupling fluid may be blown from the exposed surface of the parts while they are still in the scan nest 110. This may be done using a first gas flow port 502 attached to the pick and place mechanism 114, as shown in FIG. 5. The gas flow port 502 may be, for example, a gas knife, nozzle or point jet, or a combination thereof. In the embodiment shown in FIG. 5, the pick and place mechanism 114 comprises a vacuum manifold 128 coupled by support members 506 to a robot manipulator arm 508. Using the robot manipulator arm 508, the gas flow port 502 is moved across the parts 108 in the scan nest 110 such that gas 504 from the gas flow port 502 is directed towards the parts to remove coupling fluid from the front surfaces of the parts.

Figure 6:
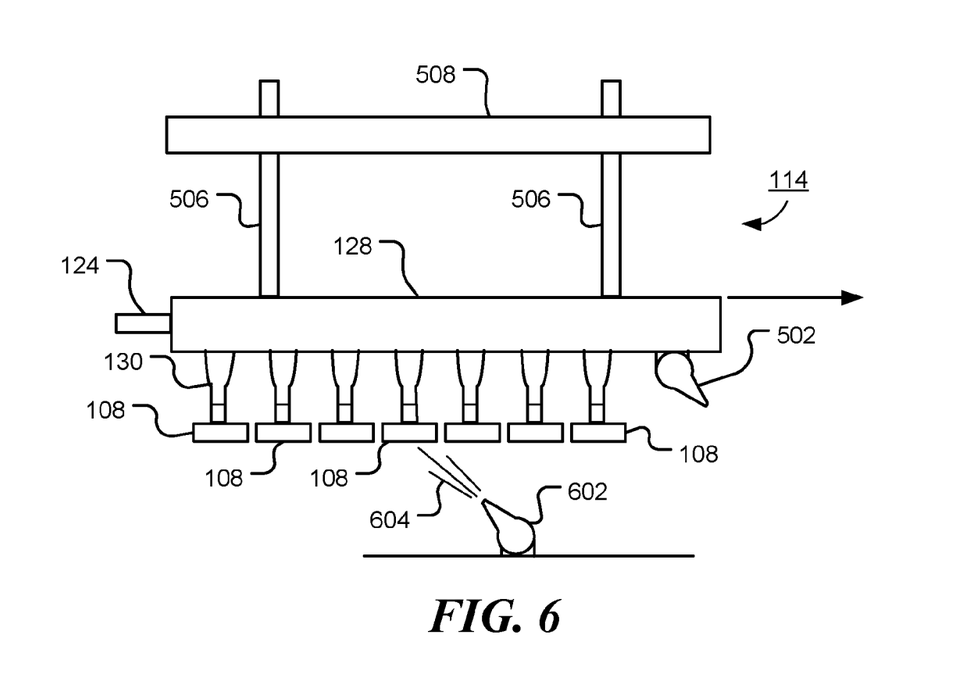
FIG. 6 is a diagrammatic view of a pick and place mechanism and a second gas flow port in accordance with some embodiments of the invention.

Once the upper surfaces of the parts have been dried, the parts are picked up by the pick and place mechanism 114, as shown in FIG. 6. The parts are then moved across a second gas flow port 602. The gas 604 from the second gas flow port 602 blows coupling fluid from the underside and edges of the parts 108.

In the embodiment shown in FIG. 5 and FIG. 6, the gas flow port 502 is attached to the pick and place mechanism 114, and moves with it. An advantage of using a gas flow port attached to the pick and place mechanism is that the flow of gas can be more accurately positioned to dry the parts more effectively. In a further embodiment of the invention, the gas flow port 502 is attached to a separate robotic arm. This arrangement allows one set of parts to be loaded or unloaded while another set of parts is being blown dry.

Figure 7:
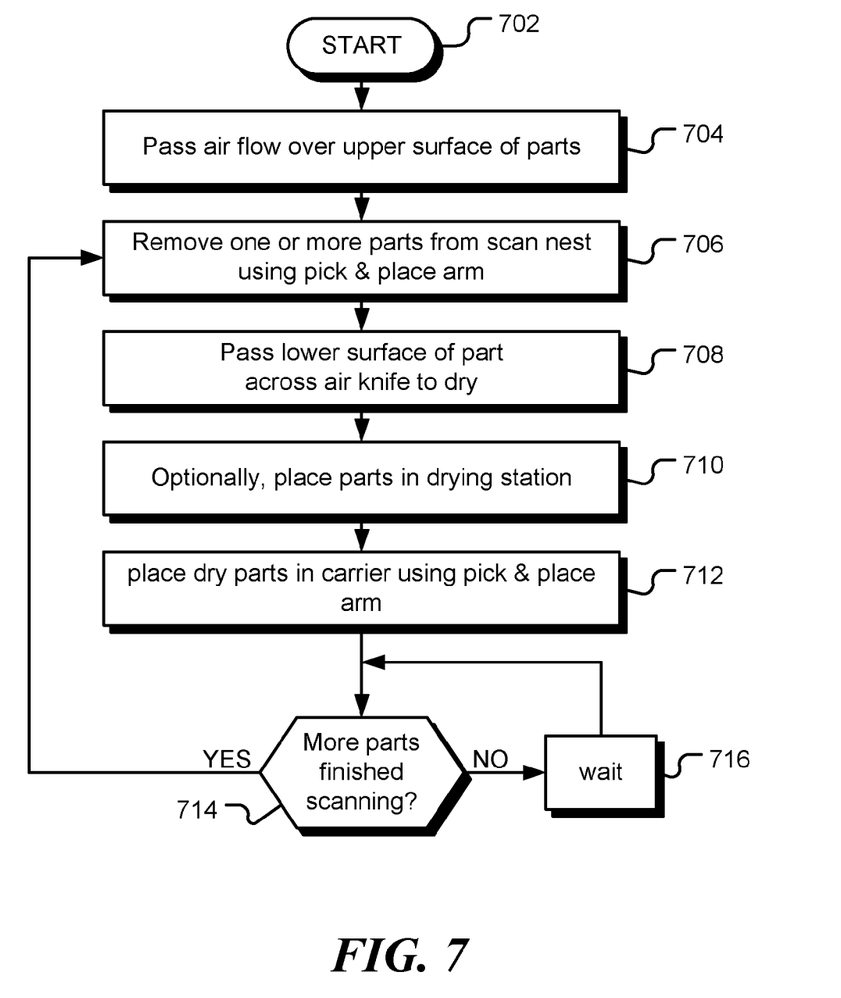
FIG. 7 is a flow chart of an exemplary method for drying scanned parts in accordance with some embodiments of the invention.

FIG. 7 is a flow chart of an exemplary method for drying scanned parts in accordance with some embodiments of the invention. As described above, coupling fluid may be used to couple ultrasound between an ultrasonic transducer of the ultrasonic scanner and the part under inspection. It is often desirable that the parts be dried once the scan has been completed. Following start block 702 in FIG. 7, a first gas flow port is used to blow gas over the exposed front surface of the parts while they are held in the scan nest at block 704. The gas flow port may be located on the pick and place mechanism or on a separate robotic arm or it may be at a fixed location close to the scan nest. At block 706, the pick and place mechanism is used to remove the scanned parts from the scan nest and, at block 708, the parts are then passed across a second gas flow port to blow coupling fluid from the back surface of the parts. Optionally, at block 710, the parts are then placed in a drying station where any residual coupling fluid is removed. At block 712 the dried parts are returned to a carrier using a pick and place mechanism. If more scanned parts are in the scan nest, as depicted by the positive branch from decision block 714, operation returns to block 706. If no more scanned parts are in the scan nest, as depicted by the negative branch from decision block 714, the system loops through wait block 716 and decision block 714 until more scanned parts are ready to be dried.

Figure 8:
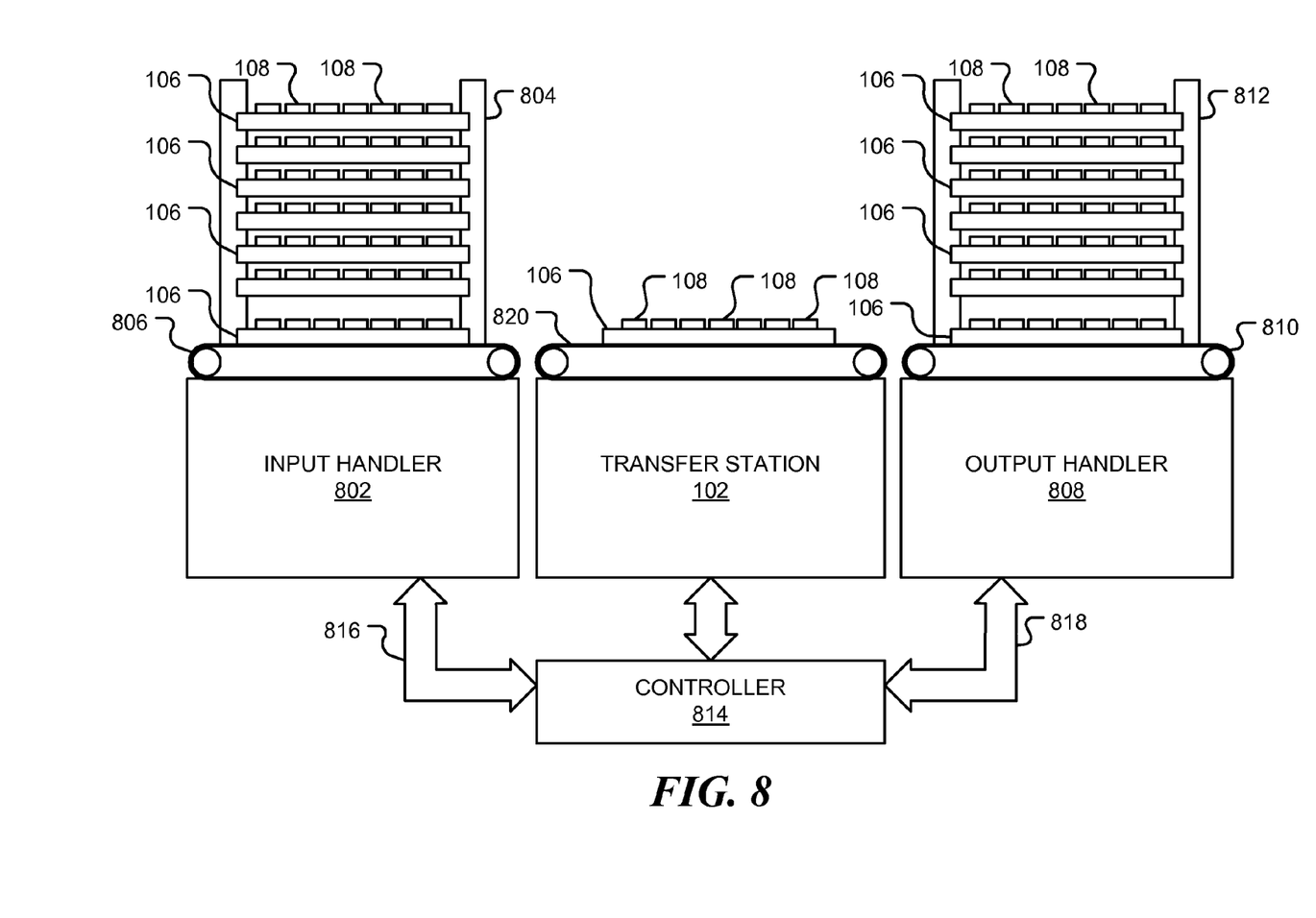
FIG. 8 is a diagrammatic representation of an exemplary ultrasonic inspection system consistent with some embodiments of the invention.

For automated inspection, the parts carrier 106 may be loaded into the transfer station 102 from an input handler, as shown in FIG. 8. Referring to the exemplary embodiment shown in FIG. 8, the input handler 802 comprises an apparatus 804 for holding a number of parts carriers 106. The apparatus 804 feeds the carriers, one at a time, to a transport mechanism 806, such as a conveyor belt, from where it is transported to the transfer station 102. Such handlers are well known to those of ordinary skill in the art. An output handler 808 may be used to receive parts carriers unloaded from the transfer station 102 after the parts 108 have been scanned. The output handler 808 comprises a transport mechanism 810, such as a conveyor belt, that receives parts carriers 106 from the transfer station 102 and loads them into an apparatus 812 for storing a number of parts carriers 106.

A controller 814 is used to control movement of the parts carriers between the input carrier 802 and the transfer station 102, and between the transfer station 102 and the output handler 808. The interface 816 between the input carrier 802 and the transfer station 102, and the interface 818 between the transfer station 102 and the output handler 808 may conform to an industry standard, such as a SMEMA, RS232 or parallel I/O standard. Similarly, the transfer station 102 may be constructed such that the conveyer 820 conforms to standards for height and other parameters to enable it to interface to any handler meeting the same standard.

Figure 9:
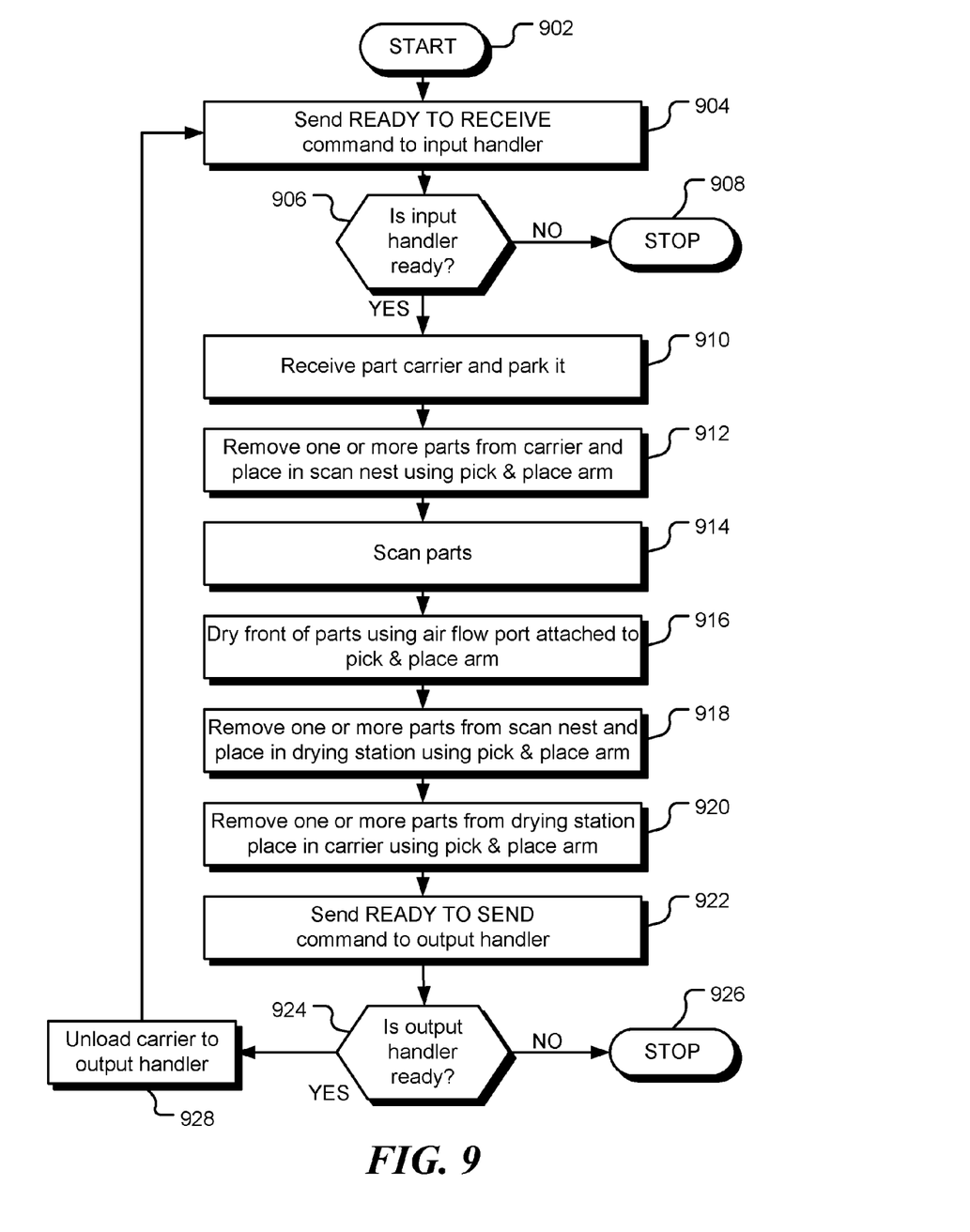
FIG. 9 is a flow chart of a method for automatic ultrasonic inspection in accordance with some embodiments of the invention.

FIG. 9 is a flow chart of a method for automatic ultrasonic inspection in accordance with some embodiments of the invention. Following start block 902 in FIG. 9, a controller of the inspection system sends a READY TO RECEIVE command at block 904 to an input handler. The input handler is an apparatus for storing and transporting parts carriers. In one embodiment, conveyor belts are used to transport the parts carrier. The conveyor in the input handler and the corresponding conveyor in the transfer station may conform to a standard mechanical equipment interface such as a SMEMA interface, specified by the Surface Mount Equipment Manufacturers Association. The SMEMA standard also specifies the electrical interface that allows the inspection system to control the handler. This enables input handler to be independent from the transfer station and allows the scanning and transfer stations to be used with any input handler conforming to the same standard.

If the input handler is not ready to respond to the READY TO RECEIVE command, as depicted by the negative branch from decision block 906, the process terminates, at least temporarily, at block 908. At block 908, an alert may be activated to alert an operator. Additionally, or alternatively, the process may send commands to the handler at intervals until the handler is ready. If the input handler is ready, as depicted by the positive branch from decision block 906, the inspection system receives a parts carrier from the input handler and parks it in the transfer station at block 910. At block 912, a group of one or more parts is removed from the parked parts carrier and placed in the scan nest of the scanning station using the pick and place mechanism. At block 914, the parts in the scan nest are scanned. At block 916, the upper surface of the parts in the scan nest is blown dry using gas from a gas flow port such as a gas knife or gas point jet attached to the pick and place mechanism. At block 918 the group of scanned parts is removed from scan nest using the pick and place mechanism and, optionally, placed in a drying station. The parts may be passed across a second gas flow port before being placed in the drying station. Once dry, the group of parts is removed from the drying station at block 920 and placed back into a parts carrier. In an alternative embodiment, the parts may be removed from the scan nest, passed over a second gas flow port and the placed directly in the parts carrier without use of a drying station.

Once all of the parts in carrier have been scanned and dried, a READY TO SEND command is sent from the controller of the inspection system to an output handler at block 922. If the output handler is not ready, as depicted by the negative branch from decision block 924, the process stops, at least temporarily at block 926. An alert may be indicated and/or the system may wait until the output handler becomes ready. If the output handler is ready, as indicted by the positive branch from decision block 924, the parts carrier is unloaded from the transfer station to the output handler at block 928. The inspection system is then ready to receive another parts carrier and flow returns to block 904.

In this manner, multiple parts in multiple parts carriers may be scanned automatically.

Figure 10:
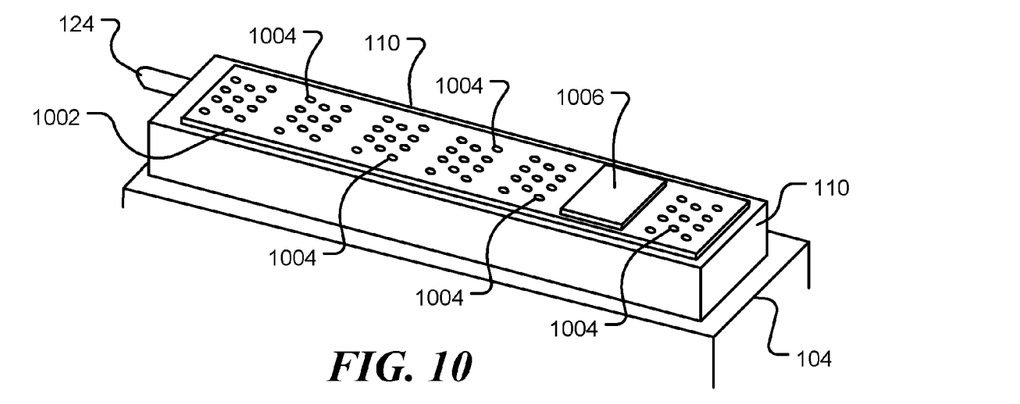
FIG. 10 is a diagrammatic view of a further scan nest in accordance with some embodiments of the invention.

FIG. 10 is a diagrammatic view of a further embodiment of a scan nest. In this embodiment a compliant layer 1002, such as natural rubber or synthetic rubber (such as silicon rubber), is located on one side of the scan nest 110. Vacuum ports 1004, pass through the compliant layer 1002 and the side of the scan nest 110 to the interior of the scan nest. When parts to be scanned (such as the part 1006 in FIG. 10) are placed on the compliant layer and cover the vacuum ports 1004, the parts are sucked into the layer as gas is drawn out through port 124 to create a low pressure inside the scan nest. A seal is formed between the compliant layer 1004 and the underside of the part 1006. In this manner the parts are held in place during the scanning process. Each part may cover one or more vacuum ports and the vacuum ports may be any shape, including, but not limited to, circles and slots. The compliant layer may comprise a single piece or multiple pieces. For example, one piece may be used for each part, or one piece used to surround each vacuum port.

Figure 11:
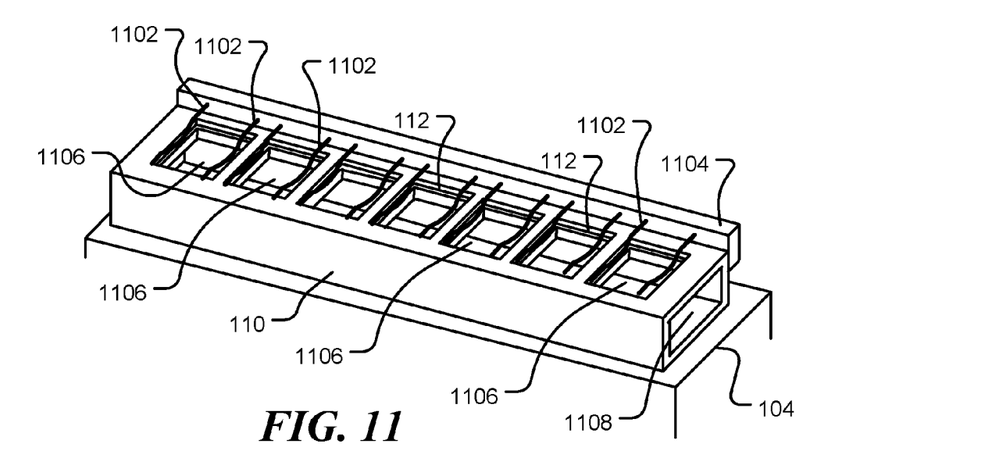
FIG. 11 is a diagrammatic view of a still further scan nest in accordance with some embodiments of the invention.

FIG. 11 is a diagrammatic view of a still further embodiment of a scan nest. In this embodiment, the parts to be scanned are held in place by spring clips or clamps 1102 that extend from a spring support member 1104 that, in turn, is coupled to the body of the scan nest 110. In one embodiment, the spring clips are positioned to hold a part on either side of a raised area to be scanned and are limited in height so as not to interfere with a scanning path. For example, the clips may hold the edges of a substrate on which a die is formed. Each part receptacle 112 has an opening 1106 to the interior of the scan nest 110. An opening 1108 in one side of the scan nest allows an ultrasound transducer to be positioned and moved below a part being scanned. This allows through-transmission scanning to be performed, where ultrasound is generated on one side of the part and the ultrasound transmitted through the part is measured on the other side of the part.

It will be appreciated that embodiments of the invention described herein may include, in addition to mechanical and electrical components, one or more conventional processors and unique stored program instructions that control the one or more processors to implement, in conjunction with certain non-processor circuits, some, most, or all of the functions of ultrasonic imaging and automated inspection described herein. The non-processor circuits may include, but are not limited to, a robot controller, signal generation and analysis circuits, signal converters, signal drivers, clock circuits, power source circuits, and user input devices. Alternatively, some or all of the processor functions could be implemented by a state machine that has no stored program instructions, or in one or more application specific integrated circuits (ASICs), in which each function or some combinations of certain of the functions are implemented as custom logic. Of course, a combination of the two approaches could be used.

Specific embodiments of the present invention have been described in the foregoing specification. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. An ultrasonic inspection system comprising:
    a transfer station that accommodates a parts carrier carrying parts to be inspected;
    a scanning station;
    a first scan nest, located in the scanning station, the first scan nest including a plurality of receptacles that accommodate a first group of parts comprising a first plurality of parts of the parts to be inspected;
    a pick and place mechanism operable to remove the first group of parts from the parts carrier in the transfer station and place the first group of parts in the first scan nest; and
    an ultrasonic scanner operable to scan the first group of parts held in the first scan nest.

2. An ultrasonic inspection system in accordance with claim 1, wherein the transfer station comprises:
    an input that receives the parts carrier from an input handler;
    an output that passes the parts carrier to an output handler; and
    a conveyor that moves the parts carrier through the transfer station from the input handler to the output handler.

3. An ultrasonic inspection system in accordance with claim 1, wherein the first scan nest further comprises:
    a part retainer operable to hold a part to be inspected in a receptacle of the plurality of receptacles, the part to be inspected being a part of the first group of parts.

4. An ultrasonic inspection system in accordance with claim 3, wherein a receptacle of the plurality of receptacles comprises a well having a ledge that supports the periphery of the part to be inspected and wherein the part retainer comprises a pump that draws air from the well through an outlet in the well to create a low pressure region that tends to retain the part to be inspected in the receptacle.

5. An ultrasonic inspection system in accordance with claim 3, wherein the part retainer comprises vacuum pump operable to generate at least a partial vacuum between the back surface of the part to be inspected and the receptacle.

6. An ultrasonic inspection system in accordance with claim 3, wherein the part retainer comprises a clamp acting on at least one side of the part to be inspected.

7. An ultrasonic inspection system in accordance with claim 6, wherein the clamp comprises one or more clamps selected from the group of clamps consisting of:
    a spring clamp,
    a piezoelectric clamp,
    a pneumatic clamp,
    a hydraulic clamp, and
    a magnetic clamp.

8. An ultrasonic inspection system in accordance with claim 1, further comprising a second scan nest wherein:
    during a first time period, the pick and place mechanism transfers a second group of parts, comprising a second plurality of parts of the parts to be inspected, from the parts carrier to the second scan nest and the ultrasonic scanner scans the first group parts in the first scan nest, and during a second time period the pick and place mechanism transfers the scanned first group of parts from the first scan nest to the parts carrier and the ultrasonic scanner scans the second group of parts in the second scan nest.

9. An ultrasonic inspection system in accordance with claim 1, wherein the first scan nest comprises a linear arrangement of a plurality of receptacles that accommodate the first group of parts.

10. An ultrasonic inspection system in accordance with claim 1, wherein the first scan nest comprises a plurality of receptacles arranged in a rectangular grid that accommodate the first group of parts.

11. An ultrasonic inspection system in accordance with claim 1, wherein the pick and place mechanism comprises a plurality of vacuum heads and wherein the spacing of the plurality of vacuum heads corresponds to the spacing of the first group of parts in the first scan nest.

12. An ultrasonic inspection system in accordance with claim 1, wherein the pick and place mechanism comprises a plurality of closely spaced vacuum heads, spaced such that, for a range of part sizes and carrier configurations, at least one vacuum head of the plurality of closely spaced vacuum heads is aligned with each of the parts in the carrier.

13. An ultrasonic inspection system in accordance with claim 1, wherein the pick and place mechanism comprises:
    a plurality of vacuum heads, and
    a vacuum saver valve that preserves the vacuum of other vacuum heads if a vacuum head of the plurality of vacuum heads fails to contact a part.

14. An ultrasonic inspection system in accordance with claim 13, wherein the pick and place mechanism further comprises a signal generator that produces a signal to indicate if a vacuum head fails to contact a part.

15. An ultrasonic inspection system in accordance with claim 14, wherein the ultrasonic scanner modifies an ultrasonic scan path in response to the signal from the signal generator of the pick and place mechanism.

16. An ultrasonic inspection system in accordance with claim 1, wherein the pick and place mechanism comprises at least one vacuum head.

17. An ultrasonic inspection system in accordance with claim 1, further comprising a computer vision system operable to determine the location of parts carried by the parts carrier, wherein the computer vision system comprises:
   vision hardware coupled to the pick and place mechanism; and
   an image analyzer in communication with control software of the pick and place mechanism.

18. An ultrasonic inspection system in accordance with claim 1, further comprising a gas flow port coupled to a robotic arm and operable to blow gas across the front surface of the first group of parts in the scan nest after the parts have been scanned.

19. An ultrasonic inspection system in accordance with claim 18, further comprising a gas flow part operable to blow gas across the back of the first group of parts held by the pick and place mechanism, after the parts have been scanned.

20. An ultrasonic inspection system in accordance with claim 1, wherein the first scan nest comprises:
   one or more vacuum ports; and
   one or more compliant layers that surround the one or more vacuum ports and support a back surface of a part to be inspected,
wherein a seal is formed between the one or more compliant layers and the back surface of the part to be inspected.

21. An ultrasonic inspection system comprising:
   a transfer station that accommodates a parts carrier carrying one or more parts to be inspected;
   a scanning station;
   a first scan nest, located in the scanning station, operable to hold the one or more parts such that the front surfaces of the parts are substantially in a first plane;
   a pick and place mechanism operable to transfer the one or more parts between the parts carrier in the transfer station and the first scan nest;
   an ultrasonic scanner operable to scan the one or more parts held in the first scan nest, the ultrasonic scanner using a coupling fluid to couple between an ultrasonic transducer and a surface of a part of the one or more parts under inspection, and
   a first gas flow port operable to move across the one or more parts in the scan nest and to blow coupling fluid from the front surface of the one or more parts after the parts have been scanned and before the parts are removed from the scan nest.

22. An ultrasonic inspection system in accordance with claim 21, further comprising a second gas flow port, wherein, after the one or more parts have been removed from the scan nest, the pick and place mechanism moves the one or more parts across the second gas flow port to blow coupling fluid from the back of the one or more parts.

23. An ultrasonic inspection system in accordance with claim 21, further comprising a drying station, wherein the pick and place mechanism moves the one or more parts from the first scan nest to the drying station after the one or more parts have been scanned.

24. An ultrasonic inspection system in accordance with claim 21, further comprising first and second drying stations, wherein the one or more parts comprise a group of a plurality of groups of parts and wherein the pick and place mechanism moves every other group of parts of the plurality of groups of parts from the scan nest to the first drying station and moves the remaining groups of parts from the first scan nest to the second drying station.

25. An ultrasonic inspection system in accordance with claim 21, wherein the first gas flow port is supported by the pick and place mechanism, and wherein the pick and place mechanism is further operable to move the first gas flow port across the one or more parts in the scan nest.

26. An ultrasonic inspection system in accordance with claim 21, wherein the first gas flow port is supported by a scanning mechanism of the ultrasonic scanner, and wherein the scanning mechanism is further operable to move the first gas flow port across the one or more parts in the scan nest.

27. A method for ultrasonic inspection of a plurality of parts, the method comprising:
   for each group of one or more parts of the plurality of parts:
      removing the group of parts from a parts carrier and placing the group of parts in a scan nest located in a scanning station using a pick and place mechanism;
      performing an ultrasonic scan of the group of parts using coupling fluid to couple ultrasound between an ultrasonic transducer and a surface of each part in the group of parts;
      blowing coupling fluid from a first surface of each part in the group of parts using a first gas flow port located on a robotic arm; and
      removing the group of parts from the scan nest using the pick and place mechanism.

28. A method in accordance with claim 27, further comprising passing the group of parts removed from the scan nest over a second gas flow port to blow coupling fluid from a second surface of each part in the group of parts.

29. A method in accordance with claim 27, wherein removing the group of parts from the scan nest comprises moving the group of parts to a drying station.

30. A method in accordance with claim 27, wherein removing the group of parts from the scan nest comprises moving the group of parts to a parts carrier.

31. A method in accordance with claim 27, wherein the pick and place mechanism comprises the robotic arm.

32. A method in accordance with claim 27, wherein the ultrasonic scan comprises a pulse-echo scan.

33. A method in accordance with claim 27, wherein the ultrasonic scan comprises a through-transmission scan.

34. A method for ultrasonic inspection of parts, the method comprising:
   removing a first group of parts, comprising a plurality of parts, from a parts carrier and placing the first group of parts in a first scan nest located in a scanning station using a pick and place mechanism;
   restraining the first group of parts in the first scan nest;
   performing an ultrasonic scan of the first group of parts;
   releasing the scanned first group of parts in the first scan nest; and
   removing the scanned first group of parts from the first scan nest using the pick and place mechanism.

35. A method in accordance with claim 34, wherein restraining the first group of parts in the first scan nest comprises applying a vacuum to the back of the parts.

36. A method in accordance with claim 34, wherein restraining the first group of parts in the first scan nest comprises creating a low pressure region between the back of the plurality of parts and the first scan nest.

37. A method in accordance with claim 34, wherein restraining the first group of parts in the first scan nest comprises applying a clamping force to one or more edges of the parts.

38. A method in accordance with claim 34, further comprising:
receiving the parts carrier from an automated input handler; and
passing the parts carrier to an automated output handler after the first group of parts have been scanned and returned to the parts carrier.

39. A method in accordance with claim 34, wherein the ultrasonic scan comprises a pulse-echo scan.

40. A method in accordance with claim 34, wherein the ultrasonic scan comprises a through-transmission scan.

41. A method in accordance with claim 34, wherein performing the ultrasonic scan comprises moving an ultrasonic transducer in a scan path that traverses the greater dimension of the first scan nest.

42. A method in accordance with claim 34, further comprising:
during a first time period:
transferring the first group of parts from the parts carrier in the first scan nest; and
performing an ultrasonic scan on a second group of parts in a second scan nest; and
during a second time period, subsequent to the first time period:
transferring the scanned second group of parts from the second scan nest to the parts carrier; and
performing the ultrasonic scan on the first group of parts in the first scan nest.

43. A method in accordance with claim 34, wherein performing an ultrasonic scan of the plurality of parts comprises moving an ultrasonic transducer across the first group of parts in the first scan nest and activating the ultrasonic transducer at intervals.

44. A method in accordance with claim 34, wherein performing an ultrasonic scan of the first group of parts comprises moving the first scan nest and the restrained first group of parts relative to an ultrasonic transducer and activating the ultrasonic transducer at intervals.

45. A method in accordance with claim 34, wherein performing an ultrasonic scan of the first group of parts comprises:
moving the first scan nest in a first direction;
moving an ultrasonic transducer in a second direction; and
activating the ultrasonic transducer at intervals.

46. A method for ultrasonic inspection of a plurality of groups of one or more parts, the method comprising:
during a first time period:
performing an ultrasonic scan of a first group of parts, of the plurality of groups of parts, in a first scan nest;
transferring a second group of scanned parts, of the plurality of groups of parts, from a second scan nest to a parts carrier; and
transferring a third group of parts, of the plurality of groups of parts, from the parts carrier to the second scan nest, and
during a second time period, subsequent to the first time period:
transferring the scanned first group of parts from the first scan nest to the parts carrier;
transferring a fourth group of parts, of the plurality of groups of parts, from the parts carrier to the first scan nest; and
performing an ultrasonic scan on the third group of parts in the second scan nest.

47. A method in accordance with claim 46, wherein performing an ultrasonic scan of the first group of parts in the first scan nest comprises:
restraining the first group of parts in the first scan nest;
moving an ultrasonic transducer in a scan path over the first group of parts; and
releasing the first group of parts from the first scan nest after the first group of parts has been ultrasonically scanned.

48. A method for ultrasonic inspection of a plurality of parts, the method comprising:
retrieving one or more parts of the plurality of parts from a parts carrier using a pick and place mechanism;
detecting if a part of the one or more of parts is missing;
moving the one or more parts to a scanning station;
performing an ultrasonic scan of the one or more parts; and
modifying the region of the ultrasonic scan if it is detected that the part of the one or more parts is missing.

49. A method in accordance with claim 48, wherein the pick and place mechanism comprises a plurality of vacuum heads, and wherein detecting if a part of the plurality of parts is missing comprises detecting if a vacuum head of the plurality of vacuum heads fails to contact the part of the plurality of parts.

50. A method in accordance with claim 49, wherein detecting if a vacuum head of the plurality of vacuum heads fails to contact the part of the plurality of parts comprises monitoring the vacuum pressure of a vacuum head of the plurality of vacuum heads.

51. A method in accordance with claim 48, wherein detecting if the part of the plurality of parts is missing comprises:
forming an image of the plurality of parts using a computer vision system; and
analyzing the image to detect parts that are present.

52. A method in accordance with claim 48, wherein detecting if the part of the plurality of parts is missing comprises:
forming an image of the plurality of parts using a computer vision system; and
analyzing the image to detect empty locations in the parts carrier.

53. A method in accordance with claim 48, further comprising detecting if a part of the one or more of parts is displaced, wherein detecting if the part of the plurality of parts is missing and detecting if a part of the one or more of parts is displaced comprises:
performing an initial ultrasonic scan of the one or more parts in the scanning station, the initial ultrasonic scan comprising at least one ultrasonic measurement for each expected part location in the scanning station; and
comparing the at least one ultrasonic measurement to an expected ultrasonic measurement.

54. A method in accordance with claim 53, further comprising aborting the ultrasonic scan if it is detected that the part of the one or more parts is displaced.

* * * * *